US011202661B1

(12) United States Patent
Rezach et al.

(10) Patent No.: US 11,202,661 B1
(45) Date of Patent: Dec. 21, 2021

(54) SURGICAL INSTRUMENT AND METHOD

(71) Applicant: Warsaw Orthopedic, Inc., Warsaw, IN (US)

(72) Inventors: William Alan Rezach, Covington, TN (US); Brian A. Butler, Millington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/085,540

(22) Filed: Oct. 30, 2020

(51) Int. Cl.
*A61B 17/70* (2006.01)

(52) U.S. Cl.
CPC ...... *A61B 17/7086* (2013.01); *A61B 17/7032* (2013.01); *A61B 17/7035* (2013.01); *A61B 17/7059* (2013.01)

(58) Field of Classification Search
CPC .................................................. A61B 17/7086
See application file for complete search history.

(56) References Cited

U.S. PATENT DOCUMENTS

| 8,216,241 | B2 * | 7/2012 | Runco ................ | A61B 17/7091 606/86 A |
| 9,050,143 | B2 * | 6/2015 | May ................... | A61B 17/7002 |
| 10,610,269 | B2 * | 4/2020 | Mickiewicz ....... | A61B 17/7082 |
| 2007/0260261 | A1 * | 11/2007 | Runco ................ | A61B 17/7091 606/104 |
| 2014/0180298 | A1 * | 6/2014 | Stevenson ............ | A61B 17/708 606/104 |
| 2014/0364912 | A1 * | 12/2014 | May ................... | A61B 17/7043 606/253 |

* cited by examiner

*Primary Examiner* — Lynnsy M Summitt
(74) *Attorney, Agent, or Firm* — Sorell, Lenna & Schmidt, LLP

(57) ABSTRACT

A surgical instrument includes spinal implant reduction instrument defining a longitudinal axis. The spinal implant reduction instrument includes a first member connected to a body. The first member includes a tapered projection configured to interlock to a first mating recess of a bone fastener. A second member is connected to the body. The second member includes a tapered projection configured to interlock to a second mating recess of the bone fastener. At least one of the members is rotatable relative to the longitudinal axis for connecting the members to the bone fastener. Systems, spinal constructs, implants and methods are disclosed.

20 Claims, 10 Drawing Sheets

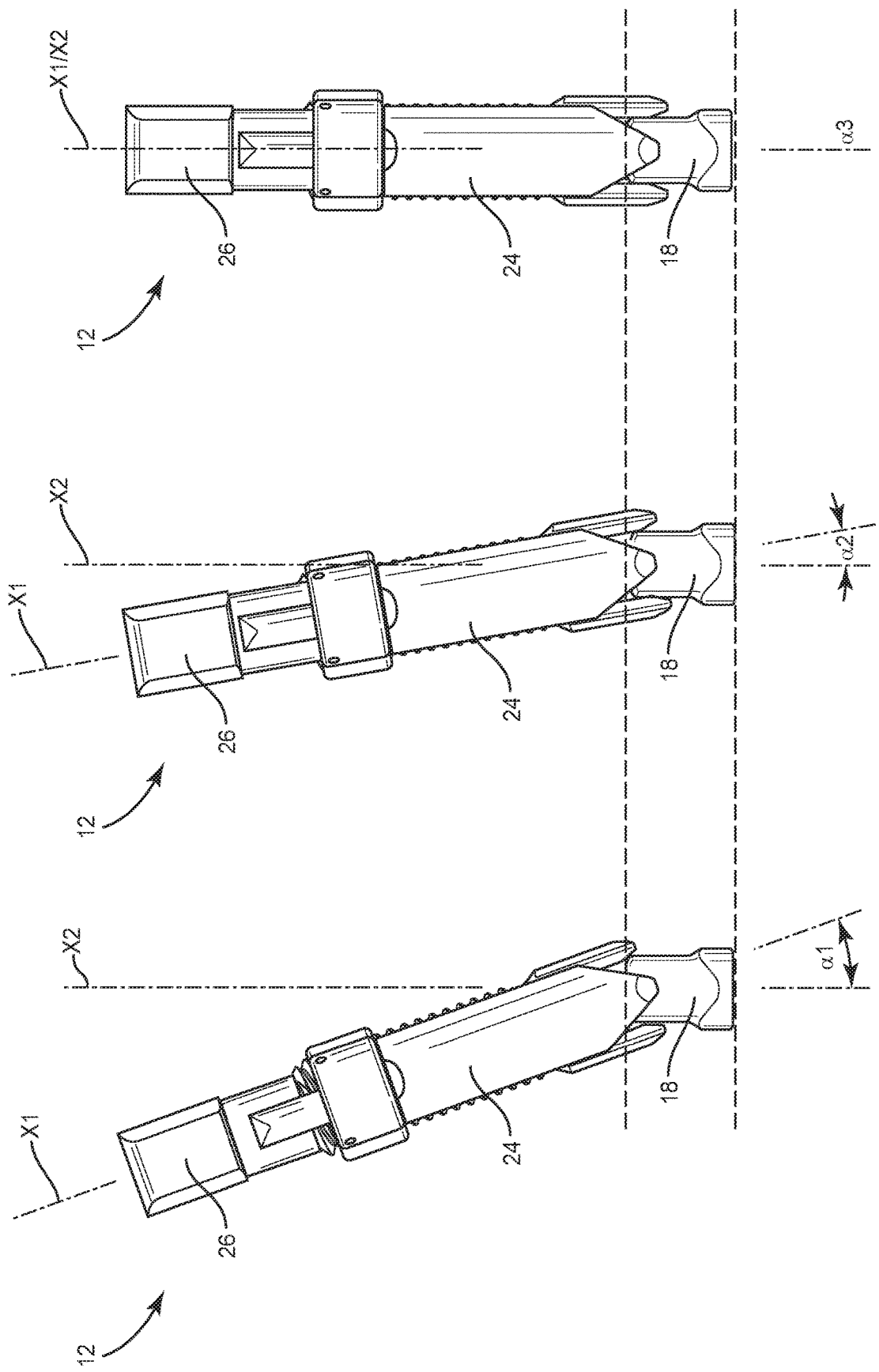

SURGICAL INSTRUMENT AND METHOD

TECHNICAL FIELD

The present disclosure generally relates to medical devices for the treatment of musculoskeletal disorders, and more particularly to a spinal implant system and a method for treating a spine.

BACKGROUND

Spinal disorders such as degenerative disc disease, disc herniation, osteoporosis, spondylolisthesis, stenosis, scoliosis, kyphosis and other curvature abnormalities, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs, which include implants such as bone fasteners, connectors, plates and vertebral rods are often used to provide stability to a treated region. These constructs can redirect stresses away from a damaged or defective region while healing takes place to restore proper alignment and generally support the vertebral members. Surgical instruments are employed, for example, to engage the fasteners for attachment of implants to the exterior of two or more vertebral members. This disclosure describes an improvement over these prior technologies.

SUMMARY

In one embodiment, a spinal implant reduction instrument is provided. The spinal implant reduction instrument defines a longitudinal axis and includes a first member connected to a body. The first member has a tapered projection configured to interlock to a first mating recess of a bone fastener. A second member is connected to the body. The second member includes a tapered projection configured to interlock to a second mating recess of the bone fastener. At least one of the members is rotatable relative to the longitudinal axis for connecting the members to the bone fastener. In some embodiments, systems, spinal constructs, implants and methods are disclosed.

In one embodiment, the spinal implant reduction instrument defines a longitudinal axis and includes a body having an inner surface that defines a cavity. A reducer is threaded to the inner surface for axial translation relative to the body. A first longitudinal member is connected to the body via a pivot and includes a tapered projection configured to interlock to a first mating recess of a bone fastener. A second longitudinal member is connected to the body via a pivot and includes a tapered projection configured to interlock to a second mating recess of the bone fastener. The members are rotatable relative to the longitudinal axis between a bone fastener capture orientation and a bone fastener release orientation.

In one embodiment, the spinal implant reduction instrument defines a longitudinal axis and includes a first member connected to a body. The first member has a tapered projection engageable to a first mating recess of a bone fastener by a dovetail connection. A second member is connected to the body. The second member includes a tapered projection engageable to a second mating recess of a bone fastener by a dovetail connection. The members are rotatable relative to the longitudinal axis between a bone fastener capture orientation and a bone fastener release orientation.

BRIEF DESCRIPTION OF THE DRAWINGS

The present disclosure will become more readily apparent from the specific description accompanied by the following drawings, in which:

FIG. 15 is a side view of components of one embodiment of a spinal implant system in accordance with the principles of the present disclosure;

FIG. 16 is a side view of the components shown in FIG. 15;

FIG. 17 is a side view of the components shown in FIG. 15; and

DETAILED DESCRIPTION

Figure 1:
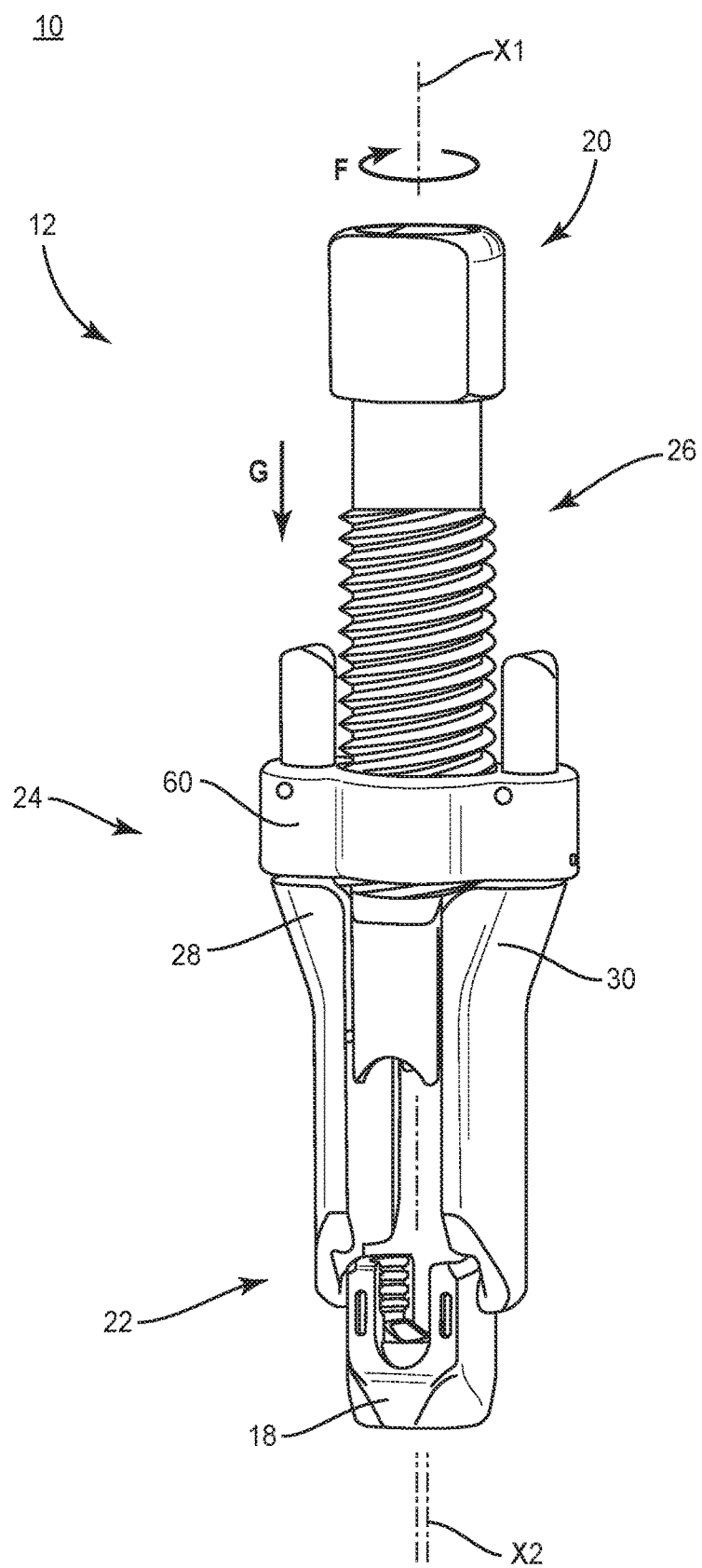
FIG. 1 is a perspective view of components of one embodiment of a spinal implant system in accordance with the principles of the present disclosure.

The exemplary embodiments of a spinal implant system and related methods of use disclosed are discussed in terms of medical devices for the treatment of musculoskeletal disorders and more particularly, in terms of a spinal implant system including one or more surgical instruments engageable with components of a spinal construct. In some embodiments, the present spinal implant system includes one or more surgical instruments and is employed with a method that facilitates connection of one or more bone fasteners and spinal rods with vertebrae to position and align one or more vertebrae for treatment of a spine. In some embodiments, the present spinal implant system includes instruments such as extenders, reducers and translators, which can be used to introduce a spinal rod to a bone fastener. In some embodiments, the surgical instrument may be used with or include a reducer assembly to introduce a spinal rod into a bone fastener. In some embodiments, the systems and methods of the present disclosure are employed with a spinal joint fusion or fixation procedure, for example, with a cervical, thoracic, lumbar and/or sacral region of a spine.

In some embodiments, the present spinal implant system includes a surgical instrument, for example, a spinal implant support configured for spinal rod reduction and use with a rod receiver of a bone fastener. In some embodiments, the spinal implant support is configured for use with a modular screw platform. In some embodiments, the spinal implant support includes a spinal rod reducer. In some embodiments, the spinal implant support defines a longitudinal axis and includes at least one arm that is rotatable relative to the axis for connecting with the rod receiver. In some embodiments, the spinal implant support includes one or more spring loaded arms.

In some embodiments, the present spinal implant system includes a spinal implant support having one or more undercut features for engagement with a rod receiver of a bone fastener. In some embodiments, the spinal implant support includes one or more arms having a lead-in chamfer configured to facilitate attachment to a rod receiver, for example, in a push down attachment configuration. In some embodiments, the spinal implant support includes one or more undercuts that engage a rod receiver of a bone fastener in a dove tail configuration. In some embodiments, the spinal implant support includes one or more undercuts that engage a rod receiver of a bone fastener in an overlap configuration.

In some embodiments, the present spinal implant system includes one or more surgical instruments and is employed with a method to perform deformity correction procedures, for example, adolescent idiopathic scoliosis and adult deformity correction procedures that require rod reduction maneuvers. In some embodiments, the spinal implant support is connectable with an attachment feature of a rod receiver of a bone fastener and includes a spinal rod reducer. In some embodiments, the attachment feature includes an undercut. In some embodiments, the undercut is configured so that the spinal implant support can overlap the rod receiver to resist and/or prevent unintended detachment of the spinal implant support from the rod receiver. In some embodiments, the spinal implant support and the attachment feature connection is configured for a secure attachment to resist and/or prevent pop-off of the spinal implant support from the rod receiver during reduction of a spinal rod with the rod receiver. In some embodiments, the attachment feature includes one or more rocker holes. In some embodiments, the attachment feature is compatible with one or more alternately configured surgical instruments, for example, alternately configured spinal reduction instruments. In some embodiments, the spinal implant support is configured for an overall low profile, for example, a low profile height and/or medial-lateral width.

In some embodiments, the present spinal implant system includes one or more surgical instruments and is employed with a method to perform rotation of the one or more surgical instruments in a sagittal plane of vertebrae to avoid surgical instrument crowding in a surgical site adjacent to a lumbar spine during surgical treatment, for example, due to lordosis or converging bone fasteners. In some embodiments, the present spinal implant system includes one or more surgical instruments that are backward compatible with existing surgical instruments disposed with vertebrae during surgical treatment.

In some embodiments, the present spinal implant system includes one or more surgical instruments and is employed with a method of surgical treatment including secure attachment of a surgical instrument defining a first axis to a rod receiver of a bone fastener defining a second axis and that allows sagittal angulation during spinal rod reduction while resisting and/or preventing pop-off of the spinal implant support from the rod receiver during reduction of a spinal rod with the rod receiver. In some embodiments, the method includes the step of initially connecting the spinal implant support to the rod receiver such that the first axis is disposed relative to the second axis at an angle in an angular range of greater than zero degrees through 20 degrees. In some embodiments, the method includes the step of initiating spinal rod reduction of the spinal rod with the rod receiver such that the first axis is disposed relative to the second axis at an angle of 10 degrees. In some embodiments, the method includes the step of finally reducing the spinal rod with the rod receiver such that the first axis is disposed relative to the second axis at an angle of 0 degrees.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, postero mid-line, direct lateral, postero-lateral, and/or anterolateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a spinal implant system including a surgical instrument, related components and methods of employing the spinal implant system in accordance with the principles of the present disclosure. Alternate embodiments are also disclosed. Reference is made in detail to the exemplary embodiments of the present disclosure, which are illustrated in the accompanying figures. Turning to FIGS. 1-18, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 can be employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of spinal implant system 10 are configured for engagement with spinal constructs, which may include spinal implants such as one or more rods, fasteners, plates and connectors. In some embodiments, the components of spinal implant system 10 are configured for engagement with existing spinal constructs attached with vertebrae in a revision surgery to manipulate tissue and/or correct a spinal disorder, as described herein.

Figure 18:
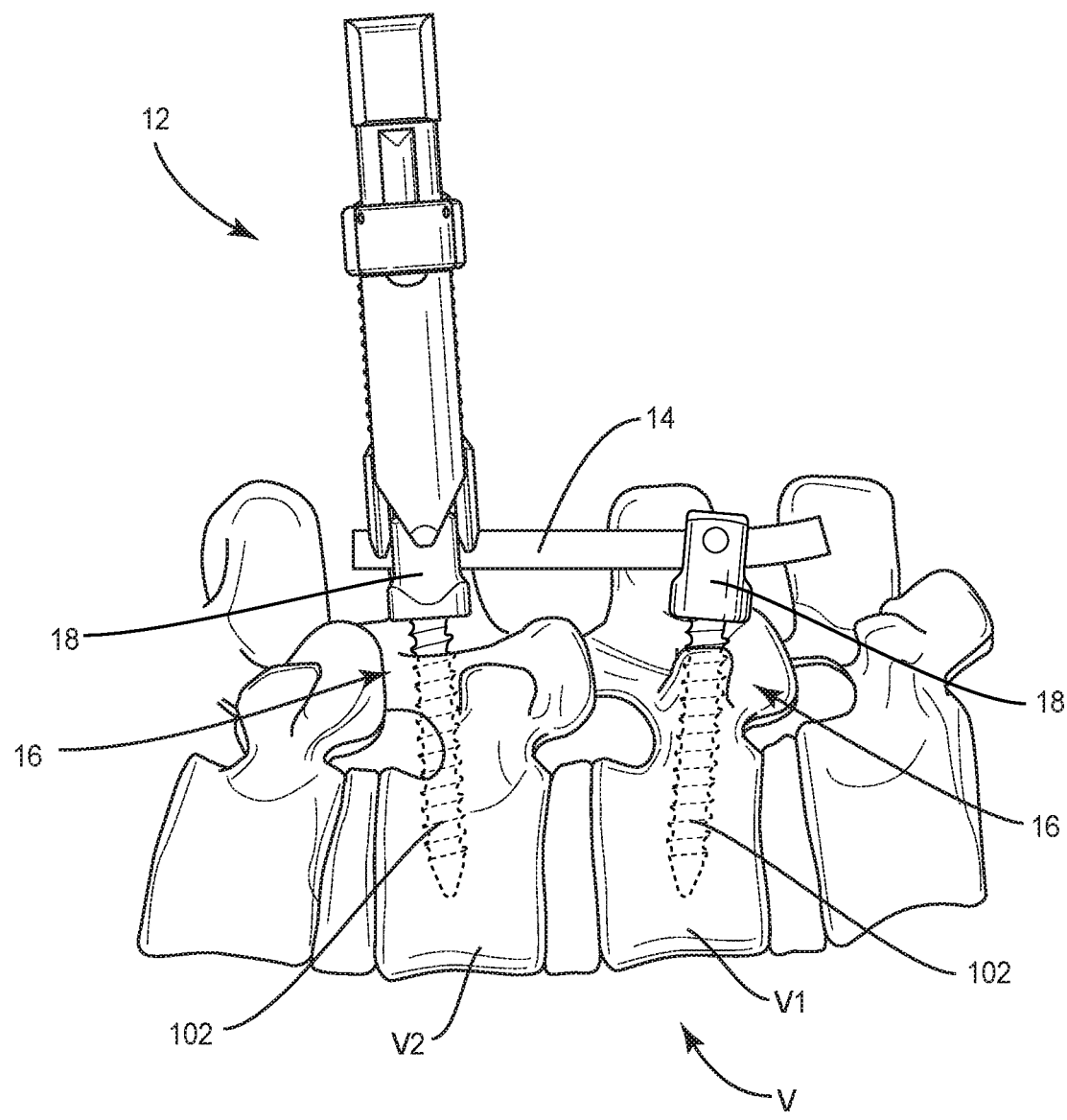
FIG. 18 is a side view of components of one embodiment of a spinal implant system in accordance with the principles of the present disclosure disposed with vertebrae.

Spinal implant system 10 includes a spinal implant reduction instrument 12. Reduction instrument 12 is configured for reduction of a spinal implant, for example, a spinal rod 14 with a rod receiver 18 of a bone fastener 16, as shown in FIG. 18. Reduction instrument 12 extends between a proximal end 20 and a distal end 22, and a defines a longitudinal axis X1, as shown in FIG. 1. In some embodiments, receiver 18 defines a longitudinal axis X2 that is in alignment with longitudinal axis X1, as shown in FIG. 1. In some embodiments, reduction instrument 12 is configured to enable sagittal angulation during rod 14 reduction while resisting and/or preventing pop-off of an implant support 24 from receiver 18 during reduction of rod 14 with receiver 18, as described herein.

Reduction instrument 12 includes implant support 24, as shown in FIG. 1. Implant support 24 is configured for connection to an attachment feature of receiver 18, as described herein and shown in FIG. 6. Implant support 24 includes a tubular body 60, members including arms 28, 30 and a rod reducer 26. Arms 28, 30 are configured for connection to tubular body 60 and reducer 26 is configured for threaded engagement to body 60, as shown in FIG. 1. In some embodiments, implant support 24 is configured for an overall low profile, for example, a low profile height and/or medial-lateral width.

Figure 2:
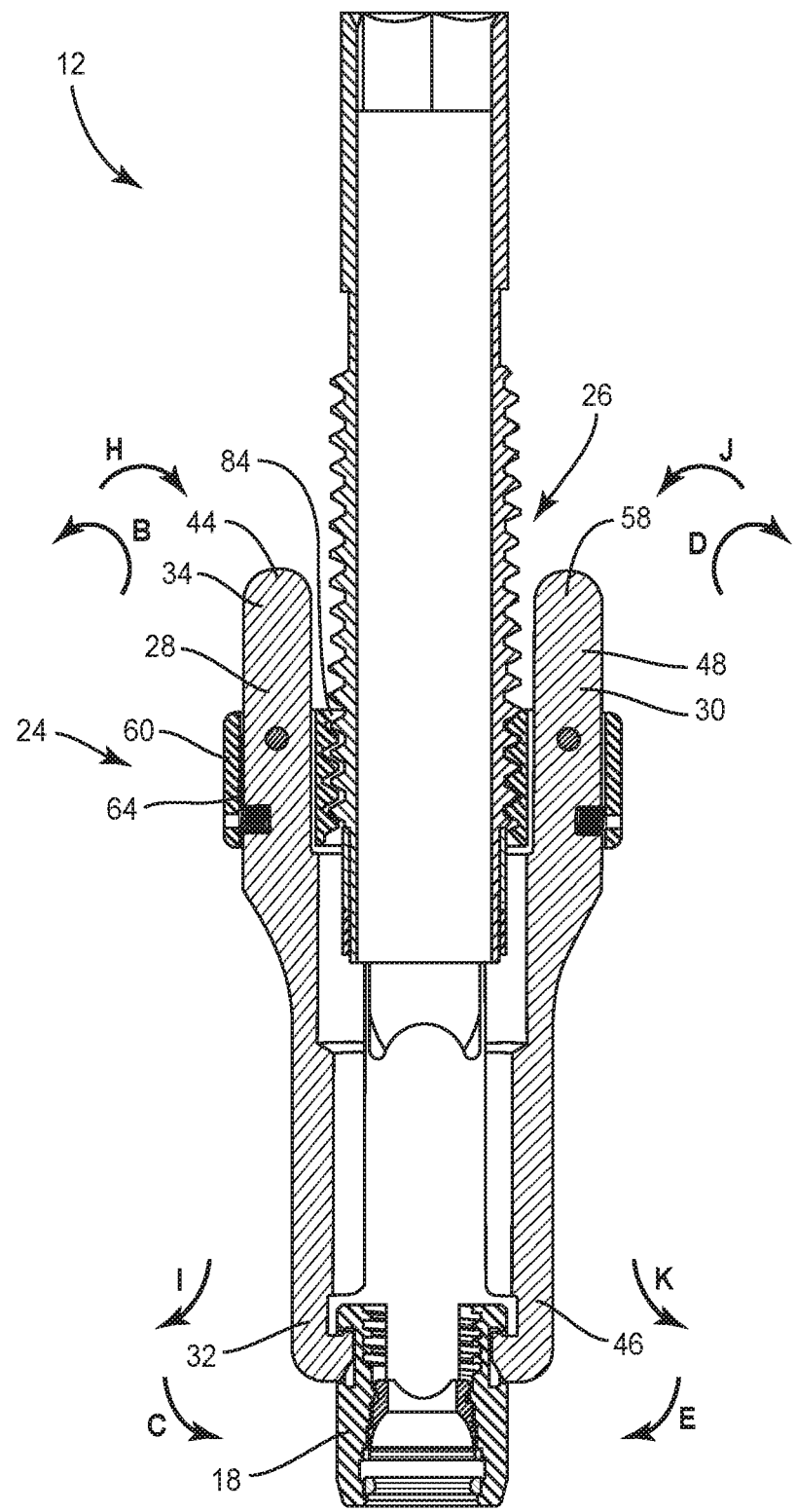
FIG. 2 is cross section view of the components shown in FIG. 1.
Figure 8:
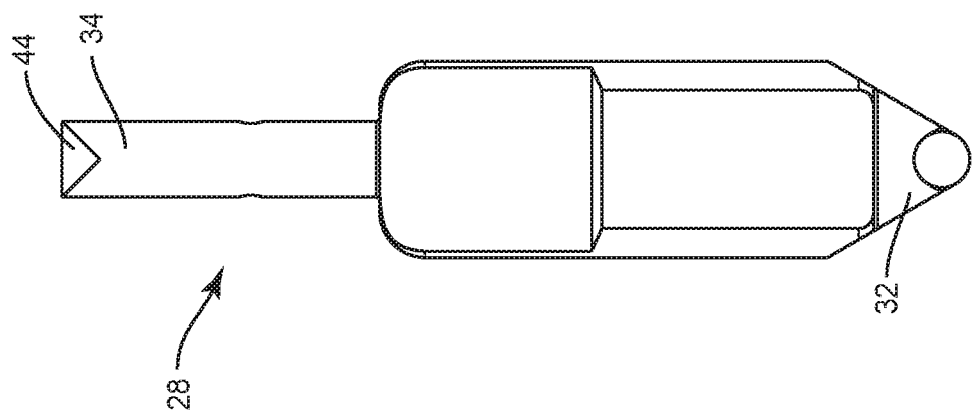
FIG. 8 is a side view of the components shown in FIG. 7.

Arms 28, 30 are rotatable, for example, independently rotatable relative to longitudinal axis X1 for connection to receiver 18. Arm 30 opposes arm 28. Arm 28 extends between a distal portion 32 and a proximal portion 34, as shown in FIGS. 2 and 8. In some embodiments, arm 28 may have various cross-section configurations, for example, oval, oblong, triangular, rectangular, square, polygonal, irregular, uniform, non-uniform, variable, tubular and/or tapered.

Figure 3:
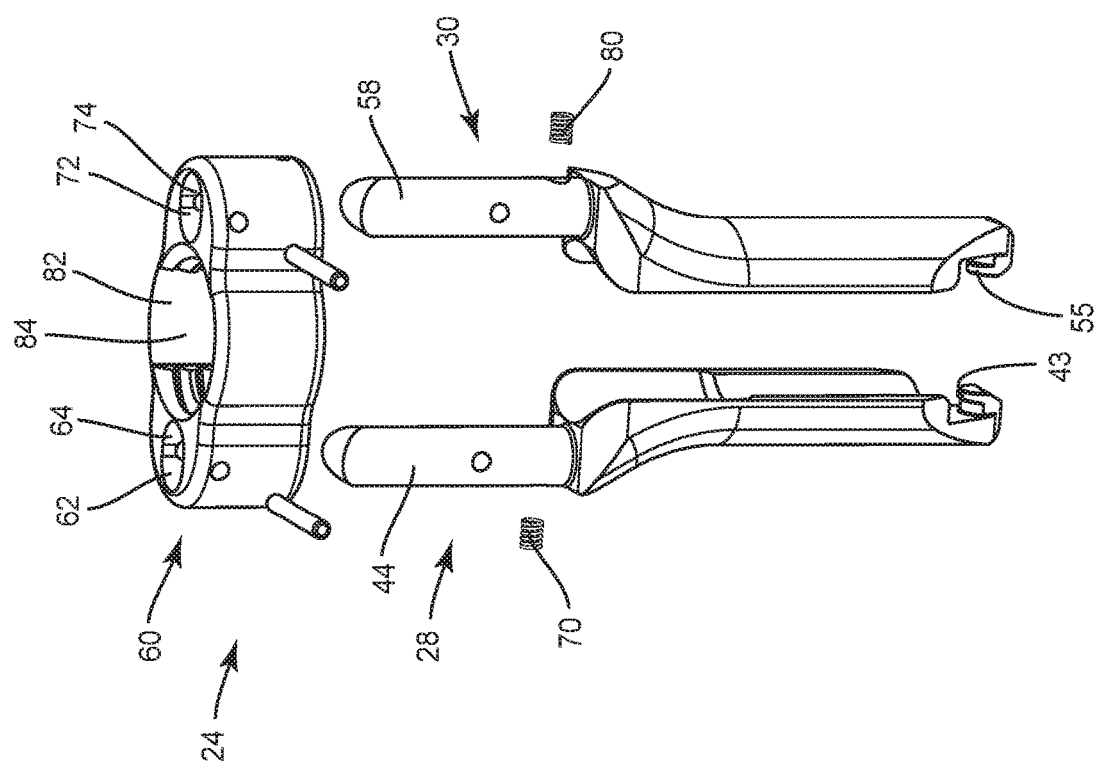
FIG. 3 is perspective view of components of one embodiment of a spinal implant system in accordance with the principles of the present disclosure with parts separated.
Figure 6:
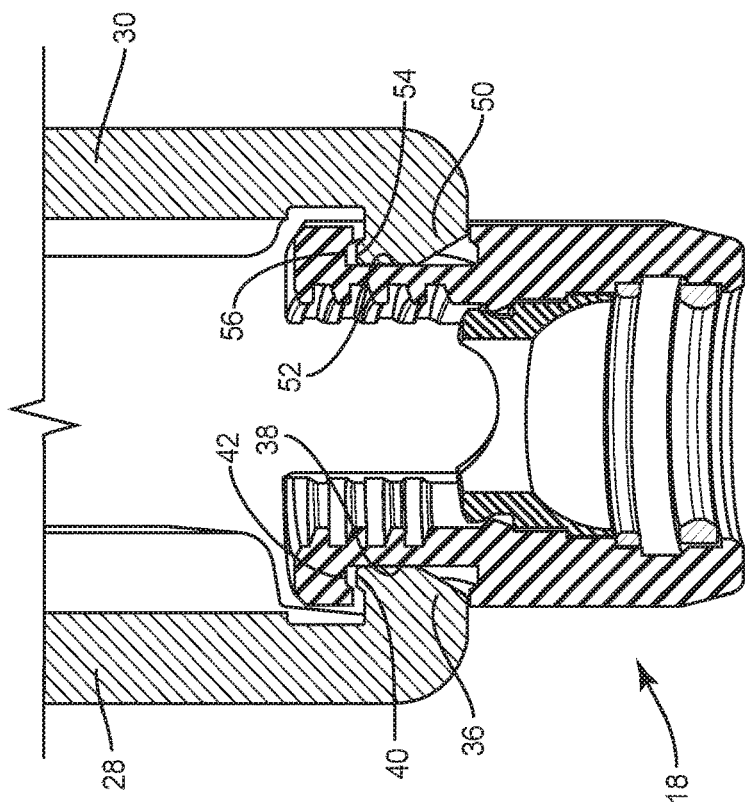
FIG. 6 is a break away view of the components shown in FIG. 2.
Figure 5:
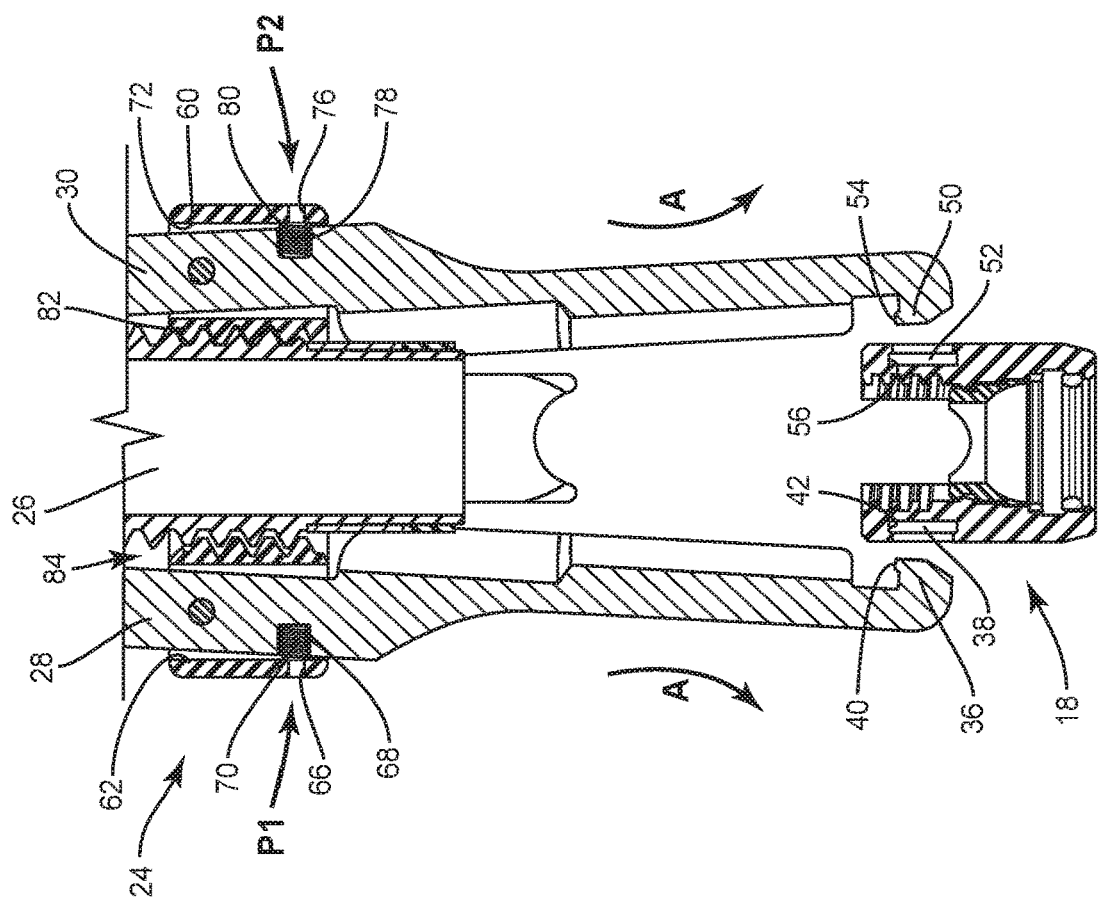
FIG. 5 is a break away view of the components shown in FIG. 2.
Figure 7:
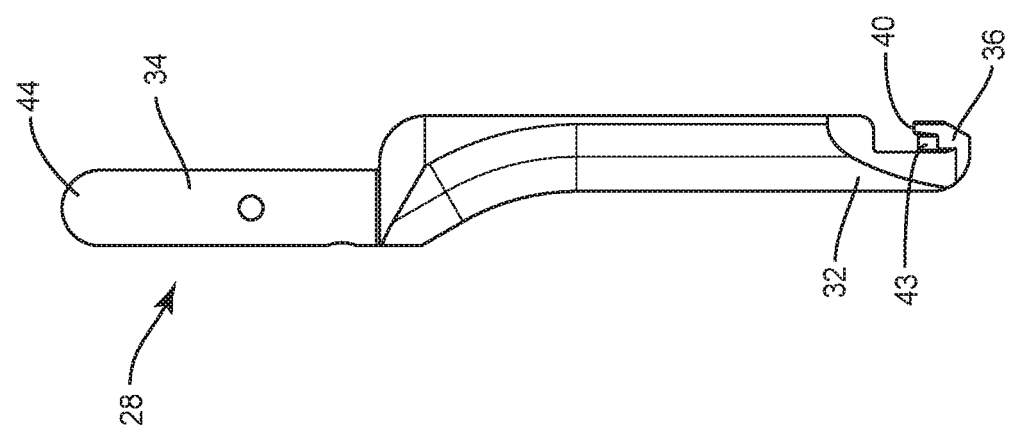
FIG. 7 is a side view of the components shown in FIG. 1.
Figure 10:
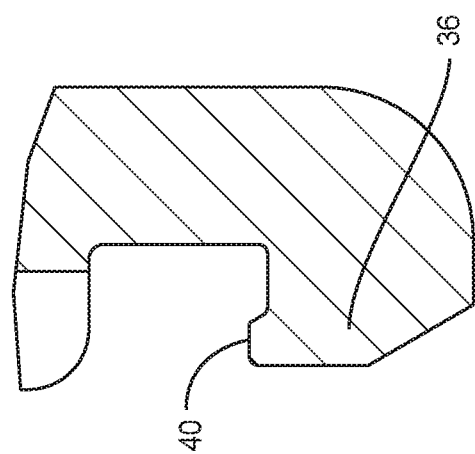
FIG. 10 is a plan view of detail Z shown in FIG. 9.
Figure 9:
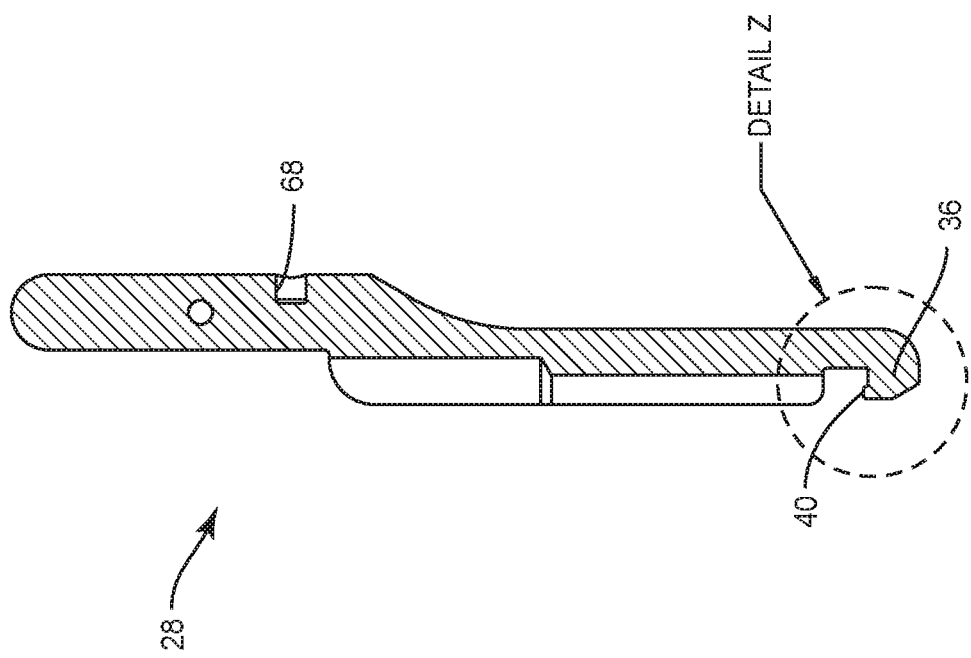
FIG. 9 is a cross section view of the components shown in FIG. 7.
Figure 11:
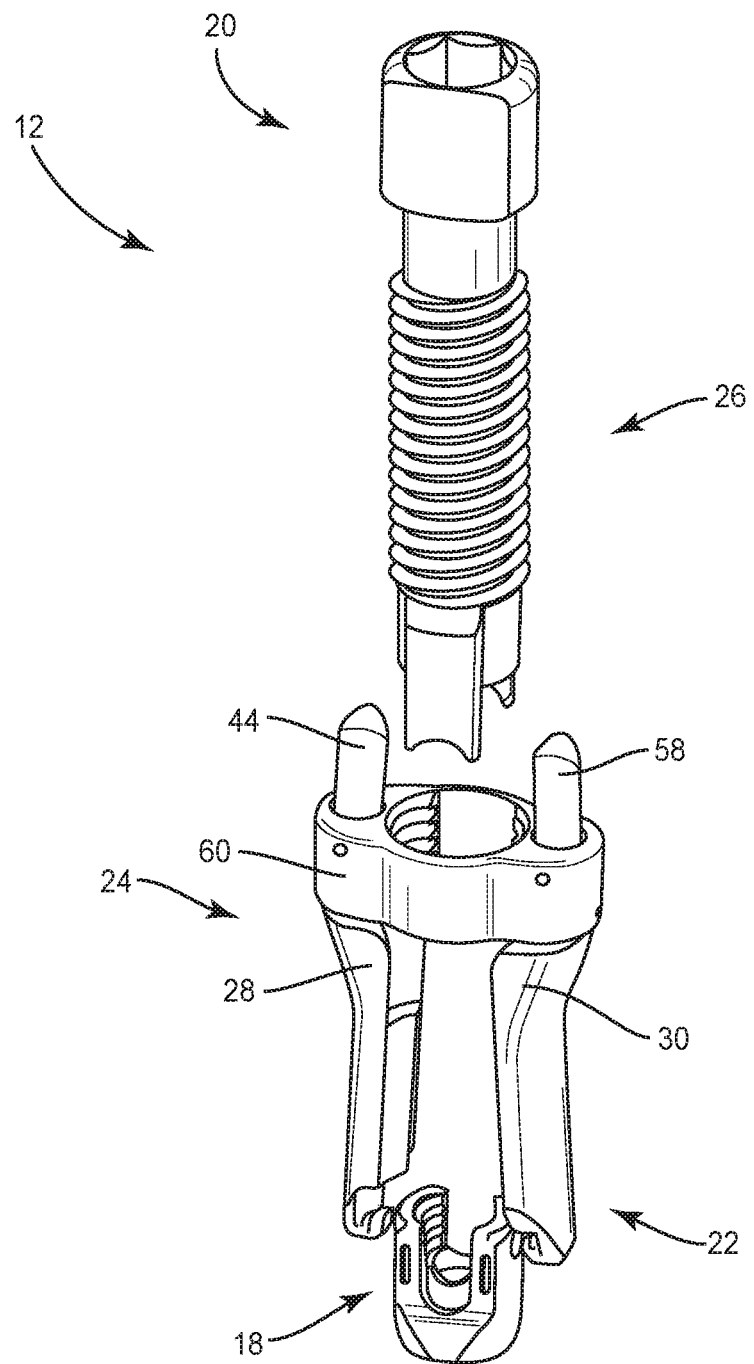
FIG. 11 is a perspective view of the components shown in FIG. 1 with parts separated.

Portion 32 includes an inner surface that defines a tapered projection 36 configured to interlock to a mating recess 38 of receiver 18, as shown in FIGS. 5 and 6. Portion 32 defines a medial-lateral width profile and projection 36 is disposed within the profile. Projection 36 engages recess 38 in a dovetail connection and the interlocked engagement between projection 36 and recess 38 secures arm 28 to receiver 18, as described herein. Projection 36 includes a hook 40, as shown in FIGS. 5-7, 9 and 10. Hook 40 is configured for engagement with an undercut surface 42 of recess 38, as shown in FIGS. 5 and 6. Engagement between hook 40 and surface 42 includes an overlap connection, as shown in FIG. 6. Surface 42 is configured such that arm 28 overlaps with receiver 18 to resist and/or prevent unintended detachment, including pop-off, of arm 28 from receiver 18 during reduction of rod 14 with receiver 18. Hook 40 includes a chamfered tip 43, as shown in FIGS. 3 and 7. Tip 43 is chamfered to facilitate attachment, including push down attachment with receiver 18.

In some embodiments, recess 38 includes a rocker hole. In some embodiments, projection 36 engages recess 38 in a snap fit engagement, a friction fit engagement, and/or a male/female engagement male/female engagement. In some embodiments, projection 36 is variously configured, for example, oval, oblong, triangular, rectangular, square, polygonal, irregular, uniform, non-uniform, variable, tubular and/or tubular. In some embodiments, tip 43 can include alternative engaging structures for example, a barb, raised elements and/or spikes to facilitate engagement of tip 43 to surface 42.

Portion 34 includes a proximal handle 44 configured for rotating projection 36 relative to longitudinal axis X1, as shown in FIG. 2. Handle 44 includes a cylindrical cross-section configuration. In some embodiments, handle 44 may have various cross-section configurations, for example, oval, oblong, triangular, rectangular, square, polygonal, irregular, uniform, non-uniform, variable, tubular and/or tapered. In some embodiments, handle 44 includes one or more of various surface configurations, such as, for example, rough, threaded, arcuate, undulating, porous, semi-porous, dimpled, polished and/or textured.

Arm 28, via handle 44, is rotatable relative to longitudinal axis X1 between a bone fastener capture orientation, as shown in FIG. 6, and a bone fastener release orientation, as shown in FIG. 5. In the bone fastener capture orientation, projection 36 engages recess 38 of receiver 18 via rotation of arm 28 in an inward direction to secure receiver 18 to reduction instrument 12. In its natural state, arm 28 is biased to the bone fastener capture orientation. Arm 28 is disposable in the bone fastener release orientation such that projection 36 disengages from recess 38 of receiver 18 via rotation of arm 28 in an outward direction to release receiver 18 from reduction instrument 12.

Arm 30 extends between a distal portion 46 and a proximal portion 48, as shown in FIG. 2. In some embodiments, arm 30 may have various cross-section configurations, for example, oval, oblong, triangular, rectangular, square, polygonal, irregular, uniform, non-uniform, variable, tubular and/or tapered.

Portion 46 includes an inner surface that defines a tapered projection 50 configured to interlock to a mating recess 52 of receiver 18, as shown in FIGS. 5 and 6. Portion 46 defines a medial-lateral width profile and projection 50 is disposed within the profile. Projection 50 engages recess 52 in a dovetail connection and the interlocked engagement between projection 50 and recess 52 secures arm 30 to receiver 18, as described herein. Projection 50 includes a hook 54, as shown in FIGS. 5 and 6. Hook 54 is configured for engagement with an undercut surface 56 of recess 52. Engagement between hook 54 and surface 56 includes an overlap connection, as shown in FIG. 6. Surface 56 is configured such that arm 30 overlaps with receiver 18 to resist and/or prevent unintended detachment, including pop-off, of arm 30 from receiver 18 during reduction of rod 14 with receiver 18. Hook 54 includes a chamfered tip 55, as shown in FIG. 3. Tip 55 is chamfered to facilitate attachment, including push down attachment to receiver 18.

In some embodiments, recess 52 includes a rocker hole. In some embodiments, projection 50 engages recess 52 in a snap fit engagement, a friction fit engagement, and/or a male/female engagement. In some embodiments, projection 50 is variously configured, for example, oval, oblong, triangular, rectangular, square, polygonal, irregular, uniform, non-uniform, variable, tubular and/or tubular. In some embodiments, tip 55 can include alternative engaging structures for example, a barb, raised elements and/or spikes to facilitate engagement of tip 55 with surface 56.

Portion 48 includes a proximal handle 58 configured for rotating projection 50 relative to longitudinal axis X1, as shown in FIG. 2. Handle 58 includes a cylindrical cross-section configuration. In some embodiments, handle 58 may have various cross-section configurations, for example, oval, oblong, triangular, rectangular, square, polygonal, irregular, uniform, non-uniform, variable, tubular and/or tapered. In some embodiments, handle 58 includes one or more of various surface configurations, such as, for example, rough, threaded, arcuate, undulating, porous, semi-porous, dimpled, polished and/or textured.

Arm 30, via handle 58, is rotatable relative to longitudinal axis X1 between the bone fastener capture orientation, as shown in FIG. 6, and the bone fastener release orientation, as shown in FIG. 5 and described herein. In the bone fastener capture orientation, projection 50 engages recess 52 of receiver 18 via rotation of arm 30 in an inward direction to secure receiver 18 to reduction instrument 12. In its natural state, arm 30 is biased to the bone fastener capture orientation. Arm 30 is disposable in the bone fastener release orientation such that projection 50 disengages from recess 52 of receiver 18 via rotation of arm 30 in an outward direction to release receiver 18 from reduction instrument 12. Portion 46 defines a medial-lateral width profile and projection 50 is disposed within the profile.

Figure 4:
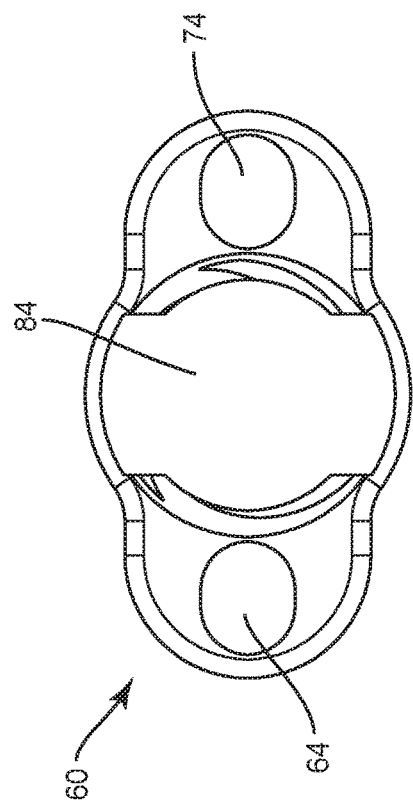
FIG. 4 is an end view of components of the system shown in FIG. 3.

Implant support 24 includes a tubular body 60 configured for connection to arms 28, 30 and engagement to reducer 26, as shown in FIG. 1. Body 60 defines an inner surface 62 that defines a cavity 64. Cavity 64 is configured for disposal of a portion of arm 28, as shown in FIGS. 2-4. In some embodiments, surface 62 of cavity 64 has one or more various surface configurations, for example, rough, threaded, arcuate, undulating, porous, semi-porous, dimpled, polished and/or textured.

Surface 62 defines a transverse opening 66, as shown in FIG. 5. Arm 28 includes a surface that defines a transverse opening 68. A spring 70 is disposed within openings 66 and 68, as shown in FIG. 5. Disposal of spring 70 within openings 66 and 68 creates a pivot point P1, as shown in FIG. 5. Arm 28 is connected to body 60 via pivot P1, and arm 28 is rotatable relative to longitudinal axis X1 between the bone fastener capture orientation and the bone fastener release orientation.

Body 60 defines an inner surface 72 that defines a cavity 74. Cavity 74 is configured for disposal of a portion of arm 30, as shown in FIGS. 2-4. In some embodiments, surface 72 of cavity 74 has one or more various surface configurations, for example, rough, threaded, arcuate, undulating, porous, semi-porous, dimpled, polished and/or textured.

Surface 72 defines a transverse opening 76, as shown in FIG. 5. Arm 30 includes a surface that defines a transverse opening 78. A spring 80 is disposed within openings 76 and 78, as shown in FIG. 5. Disposal of spring 80 within openings 76 and 78 creates a pivot point P2, as shown in FIG. 5. Arm 30 is connected to body 60 via pivot P2, and arm 30 is rotatable relative to longitudinal axis X1 between the bone fastener capture orientation and the bone fastener release orientation.

Body 60 defines a threaded inner surface 82 that defines a cavity 84. Cavity 84 is configured for threaded disposal of reducer 26 for axial translation of reducer 26 relative to body 60, as shown in FIG. 5 and described herein. Cavity 84 is disposed centrally relative to body 60 and is disposed between cavities 64 and 74. In some embodiments, surface 82 of cavity 84 has one or more various surface configurations, for example, rough, threaded, arcuate, undulating, porous, semi-porous, dimpled, polished and/or textured.

Figure 12:
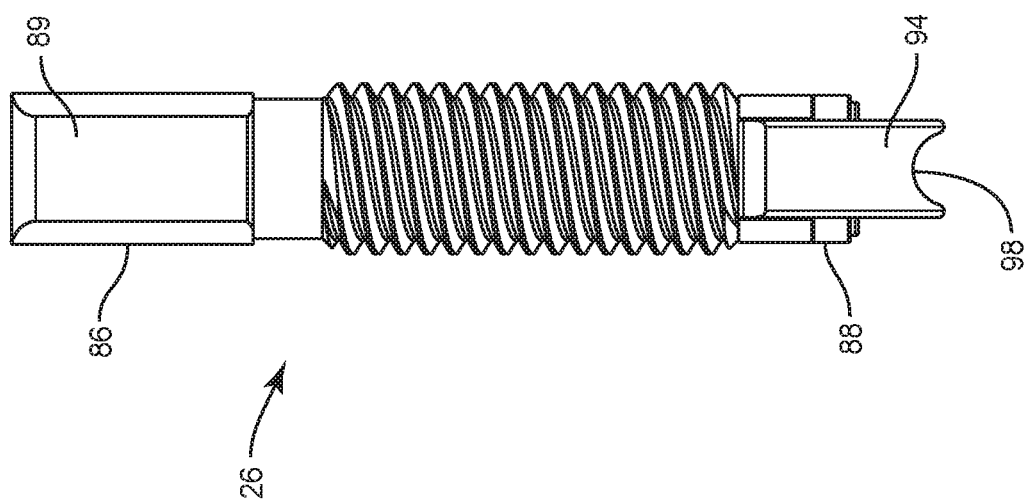
FIG. 12 is a side view of components of one embodiment of a spinal implant system in accordance with the principles of the present disclosure.

Reducer 26 is configured for threaded engagement to surface 82 that defines cavity 84 for axial translation relative to body 60 for engagement with and reduction of spinal rod 14 with receiver 18. Reducer 26 is rotated to translate reducer 26 axially, in a proximal or distal direction relative to body 60 and/or arms 28, 30. Reducer 26 extends between an end 86 and an end 88, as shown in FIG. 12. Reducer 26 has a cylindrical cross-section configuration. In some embodiments, all or only a portion of reducer 26 may have alternate cross-section configurations, for example, oval, oblong, triangular, square, polygonal, irregular, uniform, non-uniform, offset, staggered, undulating, arcuate, variable and/or tapered.

End 86 includes a handle portion 89 configured for engagement and manipulation by a user to rotate reducer 26 within cavity 84, as shown in FIG. 12. In some embodiments, handle portion 89 has one or more various surface configurations, for example, rough, threaded, arcuate, undulating, porous, semi-porous, dimpled, polished and/or textured.

Figure 13:
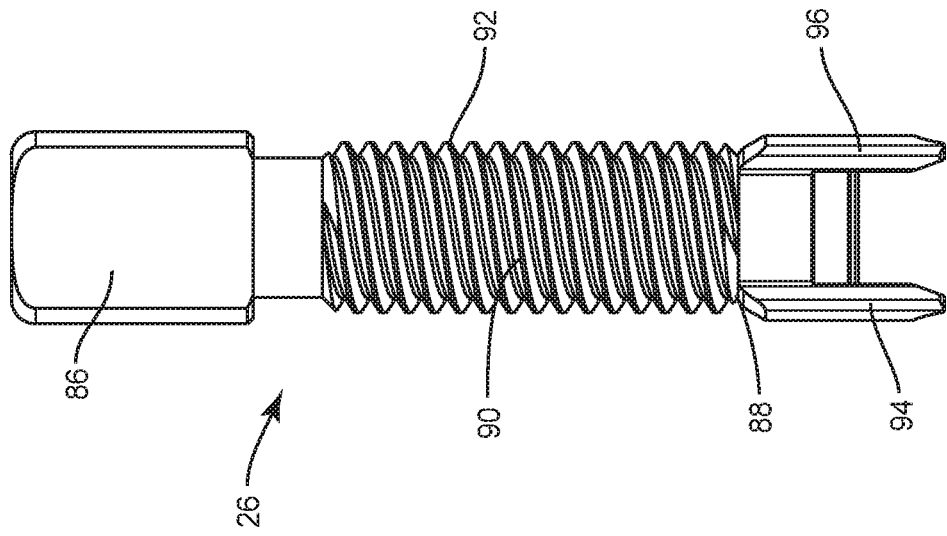
FIG. 13 a side view of the components shown in FIG. 12.

An intermediate portion 90 is disposed between end 86 and end 88, as shown in FIG. 13. Portion 90 includes a surface that defines threads 92. Portion 90, via threads 92, is configured for threaded engagement to the surface that defines cavity 84. In some embodiments, threads 92 are continuous along portion 90. In some embodiments, threads 92 may be intermittent, staggered, discontinuous and/or may include a single thread turn or a plurality of discrete threads.

Figure 14:
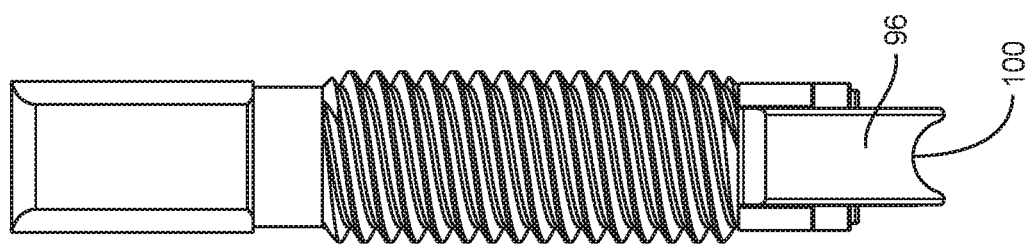
FIG. 14 is a side view of the components shown in FIG. 12.

Reducer 26 is translated such that engagement surfaces of end 88, including a tab 94 (FIG. 12) and a tab 96 (FIG. 14) engage rod 14 in a configuration to move rod 14 relative to receiver 18 to drive and/or reduce the rod 18 into receiver 14. A surface of tab 94 defines an engagement portion 98 that is shaped in an arcuate configuration, as shown in FIG. 12. Engagement portion 98 is configured for engagement to a surface of rod 14. A surface of tab 96 defines an engagement portion 100 that is shaped in an arcuate configuration, as shown in FIG. 14. Engagement portion 100 is configured for engagement to a surface of rod 14. In some embodiments, all or portions of engagement portion 98 and/or engagement portion 100 may include various configurations and/or be disposed in various orientations, such as, for example, angular, arcuate, undulating, series, parallel, offset and/or staggered.

Reduction instrument 12 allows sagittal angulation during rod 14 reduction while resisting and/or preventing pop-off of implant support 24 from receiver 18 during reduction of rod 14 with receiver 18, as shown in FIG. 18. Implant support 24 is connected to receiver 18 and disposes longitudinal axis X1 relative to longitudinal axis X2 at an angle α1 in an angular range of greater than zero degrees through 20 degrees, as shown in FIG. 15. In some embodiments, rod 14 reduction with receiver 18 disposes the longitudinal axis X1 relative to longitudinal axis X2 at an angle α2 of 10 degrees, as shown in FIG. 16. In some embodiments, final reduction of rod 14 with receiver 18 disposes longitudinal axis X1 relative to longitudinal axis X2 at an angle α3 of 0 degrees, as shown in FIG. 17.

In operation, reducer 26 is disposed within cavity 84 and arms 28, 30 are disposed in the bone fastener release orientation, including an open configuration, as shown by arrows A in FIG. 5. To position reduction instrument 12 in the bone fastener capture orientation, including a closed configuration, handle 44 of arm 28 is manually rotated in an outward direction, as shown by arrow B in FIG. 2, to translate portion 32 of arm 28 in an inward direction, as shown by arrow C in FIG. 2, to connect projection 36 of arm 28 to recess 38 of receiver 18. Handle 58 of arm 30 is manually rotated in an outward direction, as shown by arrow D in FIG. 2, to translate portion 46 of arm 30 in an inward direction, as shown by arrow E in FIG. 2, to connect projection 50 of arm 30 to recess 52 of receiver 18.

Reducer 26 is manually rotated, in a direction shown by arrow F in FIG. 1, to translate reducer 26, in a direction shown by arrow G in FIG. 1, such that tabs 94, 96 engage rod 14 to move rod 14 relative to receiver 18 to drive and/or reduce rod 18 into receiver 14, as shown in FIG. 18.

In assembly, operation and use, spinal implant system 10, is employed with a surgical procedure, such as, for example, a surgical treatment of an applicable condition or injury of an affected section of a spinal column and adjacent areas within a body. In some embodiments, spinal implant system 10 can be used in any surgical method or technique including open surgery, mini-open surgery, minimally invasive surgery and percutaneous surgical implantation, whereby vertebrae V is accessed, such as through a mini-incision, and possibly also via a sleeve (not shown) that provides a protected passageway to vertebrae V. Once access to the surgical site is obtained, the particular surgical procedure can be performed for treating the spine disorder.

An incision is made in the body of a patient and a cutting instrument (not shown) creates a surgical pathway. A preparation instrument (not shown) can be employed to prepare tissue surfaces of or surrounding vertebrae V, as well as for aspiration and irrigation of a surgical region. Pilot hole(s) (not shown) are made with the selected areas of bone, for example vertebrae V for receiving a shaft 102 of bone fastener 16, as shown in FIG. 18.

Reduction instrument 12 is disposed over receiver 18 and is in the bone fastener release orientation, including an open configuration, as shown by arrows A in FIG. 5. Handle 44 of arm 28 is manually rotated in an outward direction, as shown by arrow B in FIG. 2, to translate portion 32 of arm 28 in an inward direction, as shown by arrow C in FIG. 2, to connect projection 36 of arm 28 to recess 38 of receiver 18. Handle 58 of arm 30 is manually rotated in an outward direction, as shown by arrow D in FIG. 2, to translate portion 46 of arm 30 in an inward direction, as shown by arrow E in FIG. 2, to connect projection 50 of arm 30 to recess 52 of receiver 18 and place reduction instrument 12 in the bone fastener capture orientation, including a closed configuration.

Reducer 26 is manually rotated, in a direction shown by arrow F in FIG. 1, to translate reducer 26, in a direction shown by arrow G in FIG. 1, such that tabs 94, 96 engage rod 14 to move rod 14 relative to receiver 18 to drive and/or reduce rod 18 into receiver 14, as shown in FIG. 18. Handle 44 of arm 28 is rotated in an inward direction, as shown by arrow H in FIG. 2, to translate portion 32 of arm 28 in an outward direction, as shown by arrow I in FIG. 2, to disconnect arm 28 from receiver 18. Handle 58 of arm 30 is rotated in an inward direction, as shown by arrow J in FIG. 2, to translate portion 46 of arm 30 in an outward direction, as shown by arrow K in FIG. 2, to disconnect arm 30 from receiver 18, thereby placing reduction instrument 12 in the bone fastener release orientation.

Upon completion of a procedure, reduction instrument 12, additional surgical instruments and/or tools, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 may include one or a plurality of plates, connectors and/or bone fasteners for use with a single vertebral level or a plurality of vertebral levels. In some embodiments, one or more of bone fasteners may be engaged with tissue in various orientations, such as, for example, series, parallel, offset, staggered and/or alternate vertebral levels. In some embodiments, one or more bone fasteners may comprise multi-axial screws, sagittal angulation screws, pedicle screws, monoaxial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant reduction instrument defining a longitudinal axis, the instrument comprising:
 a body defining first and second channels and including an inner surface defining a passageway positioned between the channels, the passageway having a maximum length along the axis equal to a maximum length of the first channel along the axis and a maximum length of the second channel along the axis, the inner surface defining a female thread configured for engagement with a male thread of a reducer;
 a first member comprising a proximal end disposed in the first channel and a distal end including a tapered projection configured to interlock to a first mating recess of a bone fastener; and
 a second member comprising a proximal end disposed in the second channel and a distal end including a tapered projection configured to interlock to a second mating recess of the bone fastener,
 at least one of the members being rotatable relative to the longitudinal axis for connecting the members to the bone fastener.

2. A spinal implant reduction instrument as recited in claim 1, wherein the projection of the first member engages the first mating recess by a dovetail connection.

3. A spinal implant reduction instrument as recited in claim 1, wherein the projection of the first member includes a hook.

4. A spinal implant reduction instrument as recited in claim 3, wherein the first mating recess includes an undercut surface engageable with the hook in an overlap connection.

5. A spinal implant reduction instrument as recited in claim 3, wherein the hook includes a chamfered tip.

6. A spinal implant reduction instrument as recited in claim 1, wherein the first member and the second member are independently rotatable relative to the longitudinal axis.

7. A spinal implant reduction instrument as recited in claim 1, wherein the first member is rotatable relative to the longitudinal axis between a bone fastener capture orientation and a bone fastener release orientation.

8. A spinal implant reduction instrument as recited in claim 7, wherein the first member is biased to the bone fastener capture orientation.

9. A spinal implant reduction instrument as recited in claim 1, wherein the channels and the passageway each extend through opposite proximal and distal surfaces of the body.

10. A spinal implant reduction instrument as recited in claim 1, wherein the body includes a non-threaded outer surface opposite the inner surface.

11. A spinal implant reduction instrument as recited in claim 1, wherein the body includes an outer surface opposite the inner surface, the first channel being positioned entirely between the passageway and the outer surface such that the first channel is spaced apart from the passageway, the second channel being positioned entirely between the passageway and the outer surface such that the second channel is spaced apart from the passageway.

12. A spinal implant reduction instrument as recited in claim 1, wherein the body includes a second inner surface defining the first channel and a third inner surface defining the second channel, the second inner surface extending 360 degrees about a portion of the proximal end of the first member, the third inner surface extending 360 degrees about a portion of the proximal end of the second member.

13. A spinal implant reduction instrument as recited in claim 1, wherein the first member extends along a second longitudinal axis between the proximal end of the first member and the distal end of the first member, the distal end of the first member including an arm extending parallel to the second longitudinal axis, the projection of the first member extending outwardly directly from an outer surface of the arm.

14. A spinal implant reduction instrument as recited in claim 1, wherein the first member extends along a second longitudinal axis between the proximal end of the first member and the distal end of the first member, the proximal end of the first member extending parallel to the second longitudinal axis from a proximal end surface of the first member to an interface between the proximal end of the first member and the distal end of the first member.

15. A spinal implant reduction instrument defining a longitudinal axis, the instrument comprising:
 a body defining first and second channels and including an inner surface that defines a passageway positioned between the channels, the passageway having a maximum length along the axis equal to a maximum length of the first channel along the axis and a maximum length of the second channel along the axis, the inner surface defining a female thread;

a reducer comprising a male thread threaded with the female thread for axial translation relative to the body;

a first longitudinal member comprising a proximal end disposed in the first channel, the first member being connected to the body via a first pivot, the first member comprising a distal end including a tapered projection configured to interlock to a first mating recess of a bone fastener; and a second longitudinal member comprising a proximal end disposed in the second channel, the second member being connected to the body via a second pivot, the second member comprising a distal end including a tapered projection configured to interlock to a second mating recess of the bone fastener, the members being rotatable relative to the longitudinal axis between a bone fastener capture orientation and a bone fastener release orientation.

16. A spinal implant reduction instrument as recited in claim 15, wherein the projection of the first member includes a hook and the projection of the second member includes a hook.

17. A spinal implant reduction instrument as recited in claim 16, wherein the mating recesses include an undercut surface engageable with the respective hooks of the members in an overlap connection.

18. A spinal implant reduction instrument as recited in claim 15, wherein the members are biased to the bone fastener capture orientation.

19. A spinal implant reduction instrument defining a longitudinal axis, the instrument comprising:

a body defining first and second channels and including an inner surface defining a passageway positioned between the channels, the passageway having a maximum length along the axis equal to a maximum length of the first channel along the axis and a maximum length of the second channel along the axis, the inner surface defining a female thread configured for engagement with a male thread of a reducer;

a first member comprising a proximal end disposed in the first channel and a distal end including a tapered projection engageable to a first mating recess of a bone fastener by a dovetail connection; and a second member comprising a proximal end disposed in the second channel and a distal end including a tapered projection engageable to a second mating recess of a bone fastener by a dovetail connection, the members being rotatable relative to the longitudinal axis between a bone fastener capture orientation and a bone fastener release orientation.

20. A spinal implant reduction instrument as recited in claim 19, wherein the members are biased to the bone fastener capture orientation.

\* \* \* \* \*